(12) United States Patent
Chang

(10) Patent No.: US 9,024,764 B2
(45) Date of Patent: May 5, 2015

(54) METHOD AND APPARATUS FOR MANIPULATING DRIVER CORE TEMPERATURE TO ENHANCE DRIVER ALERTNESS

(75) Inventor: Hsuan Chang, Mountain View, CA (US)

(73) Assignee: Honda Motor Co., Ltd., Tokyo (JP)

(*) Notice: Subject to any disclaimer, the term of this patent is extended or adjusted under 35 U.S.C. 154(b) by 1052 days.

(21) Appl. No.: 12/017,635

(22) Filed: Jan. 22, 2008

(65) Prior Publication Data
US 2008/0180235 A1 Jul. 31, 2008

Related U.S. Application Data

(60) Provisional application No. 60/886,653, filed on Jan. 25, 2007.

(51) Int. Cl.
G08B 23/00 (2006.01)
A61B 5/18 (2006.01)
A61B 5/01 (2006.01)
A61B 5/16 (2006.01)

(52) U.S. Cl.
CPC ... *A61B 5/18* (2013.01); *A61B 5/01* (2013.01); *A61B 5/165* (2013.01)

(58) Field of Classification Search
USPC ............ 340/449, 575, 573.1, 574, 576; 600/300, 483, 549; 701/1
See application file for complete search history.

(56) References Cited

U.S. PATENT DOCUMENTS 3,234,409 A * 2/1966 March et al. .................. 307/141
4,509,531 A * 4/1985 Ward ............................. 600/549
5,018,521 A * 5/1991 Campbell ...................... 607/98
5,259,553 A 11/1993 Shyu
5,441,476 A 8/1995 Kitado et al.
(Continued)

FOREIGN PATENT DOCUMENTS

DE 10252765 A1 * 5/2004
JP H05-3919 A 1/1993
(Continued)

OTHER PUBLICATIONS

Takchito et al, (2002) Detecting drowsiness while driving by measuring eye movement, IEEE, p. 156.*
(Continued)

*Primary Examiner* — Paul Obiniyi
(74) *Attorney, Agent, or Firm* — Fenwick & West LLP; Mark E. Duell

(57) ABSTRACT

The present invention provides a system, method and apparatus for reducing a vehicle driver's core temperature to offset drowsiness. In one embodiment, a temperature sensor records data describing a vehicle driver core temperature and communicates the data describing the vehicle driver core temperature to a temperature regulator. The temperature regulator determines whether the vehicle driver core temperature is similar to one or more circadian temperatures associated with wakefulness. If the vehicle driver core temperature is similar to a circadian temperature associated with sleep, the temperature regulator reduces the vehicle driver core temperature. In an embodiment the temperature regulator cools a material physically contacting the venous plexuses or arteriovenous anastomoses to cool the portions of the vehicle driver's anatomy which most efficiently cool the vehicle driver.

18 Claims, 7 Drawing Sheets

(56) References Cited

U.S. PATENT DOCUMENTS

| | | | |
|---|---|---|---|
| 5,689,241 A * | 11/1997 | Clarke et al. | 340/575 |
| 5,982,287 A | 11/1999 | Brannen et al. | |
| 6,091,334 A | 7/2000 | Galiana et al. | |
| 6,149,674 A | 11/2000 | Borders | |
| 6,218,947 B1 | 4/2001 | Sutherland | |
| 6,313,749 B1 * | 11/2001 | Horne et al. | 340/575 |
| 6,454,707 B1 * | 9/2002 | Casscells et al. | 600/300 |
| 6,509,552 B1 * | 1/2003 | Roske et al. | 219/497 |
| 6,602,277 B2 | 8/2003 | Grahn et al. | |
| 6,656,208 B2 | 12/2003 | Grahn et al. | |
| 6,846,322 B2 | 1/2005 | Kane et al. | |
| 6,950,027 B2 * | 9/2005 | Banas | 340/576 |
| 6,974,442 B2 | 12/2005 | Grahn et al. | |
| 7,187,960 B2 * | 3/2007 | Abreu | 600/310 |
| 2002/0101354 A1 | 8/2002 | Banas | |
| 2003/0032870 A1 * | 2/2003 | Farwell | 600/300 |
| 2003/0040783 A1 * | 2/2003 | Salmon | 607/111 |
| 2003/0078714 A1 * | 4/2003 | Kitano et al. | 701/41 |
| 2003/0092975 A1 | 5/2003 | Casscells et al. | |
| 2003/0181815 A1 * | 9/2003 | Ebner et al. | 600/483 |
| 2004/0152957 A1 | 8/2004 | Stivoric et al. | |
| 2004/0201481 A1 * | 10/2004 | Yoshinori et al. | 340/575 |
| 2004/0242976 A1 * | 12/2004 | Abreu | 600/315 |
| 2004/0243013 A1 * | 12/2004 | Kawachi et al. | 600/509 |
| 2004/0261567 A1 * | 12/2004 | Menaldo et al. | 74/522 |
| 2005/0209663 A1 * | 9/2005 | Hamilton et al. | 607/108 |
| 2005/0251118 A1 * | 11/2005 | Anderson et al. | 606/9 |
| 2005/0277815 A1 * | 12/2005 | Taniguchi et al. | 600/300 |
| 2006/0038447 A1 * | 2/2006 | Bruelle-Drews | 307/10.1 |
| 2006/0122673 A1 * | 6/2006 | Callister et al. | 607/105 |
| 2006/0167595 A1 * | 7/2006 | Breed et al. | 701/1 |
| 2006/0293608 A1 | 12/2006 | Rothman et al. | |
| 2007/0161921 A1 * | 7/2007 | Rausch | 600/549 |
| 2007/0270393 A1 * | 11/2007 | Buckley et al. | 514/171 |
| 2008/0021531 A1 * | 1/2008 | Kane et al. | 607/111 |
| 2008/0146892 A1 * | 6/2008 | LeBoeuf et al. | 600/300 |

FOREIGN PATENT DOCUMENTS

| | | | |
|---|---|---|---|
| JP | H05-3920 A | 1/1993 |
| JP | H05-15595 A | 1/1993 |
| JP | H07-225042 A | 8/1995 |
| JP | H08-89578 A | 4/1996 |
| JP | 2003-010230 A | 1/2003 |
| JP | 2004-290499 A | 10/2004 |

OTHER PUBLICATIONS

Ayoob et al. A user centered drowsy-driver detection and warning system, (2003) ACM.*

Jodie et al. Human Physiologiccal response to cold exposure (2004), Aviation, space and environmental Medicine, vol. 75, No. 5.*

H. W. Wilson "Heat illness prevention goes high tech: The Physician and Sportsmedicine", V. 31, No. 8, (Aug. 2003) p. 2, 6, 14.*

Dennis .A. Grahn et al., *Heat Extraction through the Palm of one Hand Improves Aerobic Exercise Endurance in a Hot Environment*, Journal of Applied Physiology, May 5, 2005, pp. 972-978, vol. 99.

Richard Grace et al., *Drowsy Driver Monitor and Warning System*, [online] retrieved on May 8, 2008, pp. 1-5, Retrieved from URL:< http://ppc.uiowa.edu/Driving-Assessment/2001/Summaries/Driving%20Assessment%20Papers/11_Grace_Richard.htm>.

European Patent Office Supplementary Partial European Search Report, European Patent Application No. 08728162.2, Dec. 10, 2009, 4 pages.

PCT International Search Report and Written Opinion, PCT/US2008/051830, May 23, 2008, 9 Pages.

European Patent Office, Examination Report, European Patent Application No. 08728162.2, Oct. 15, 2010, seven pages.

European Patent Office, Examination Report, European Patent Application No. 08728162.2, Oct. 23, 2010, four pages.

* cited by examiner

METHOD AND APPARATUS FOR MANIPULATING DRIVER CORE TEMPERATURE TO ENHANCE DRIVER ALERTNESS

RELATED APPLICATIONS

This application claims priority from U.S. Provisional Application No. 60/886,653, filed on Jan. 25, 2007, which is incorporated by reference herein in its entirety.

FIELD OF THE INVENTION

This invention relates generally to driver and vehicle safety, and more particularly to reducing a vehicle driver's core temperature to inhibit drowsiness.

BACKGROUND OF THE INVENTION

When a person becomes drowsy, alertness and responsiveness are reduced. However, people often become drowsy when operating a vehicle for a prolonged period of time. Hence, drowsiness causes many accidents during vehicle operation, such as driving. In particular, after driving for long periods, vehicle drivers often become drowsy and fail to promptly react to adverse situations. This increased response time can cause loss of vehicular control leading to an accident.

Because of the risks of driving or otherwise operating a vehicle while drowsy, conventional safety systems attempt to keep a vehicle driver awake. Many of these conventional methods monitor the frequency in which a vehicle driver's eyelids open and close or measure the eye activity of a vehicle driver to detect signs of drowsiness. Responsive to detecting signs of drowsiness, these conventional safety systems sound an alarm or take another action to alert or startle the vehicle driver.

However, these conventional safety systems only briefly increase vehicle driver alertness. Because these systems only increase driver alertness for a short period of time vehicle drivers frequently become drowsy again if driving or vehicle operation continues. Additionally, vehicle drivers can become desensitized to the alert after it repeatedly occurs, reducing the long-term effectiveness of the alert.

Hence, there is a need for a method and apparatus to reduce vehicle driver drowsiness for more than a short period of time.

SUMMARY OF THE INVENTION

The present invention provides a system, method and apparatus for reducing a vehicle driver's core temperature to offset drowsiness. In one embodiment, a temperature sensor, such as a thermometer, records data describing a vehicle driver core temperature. The temperature sensor communicates the data describing the vehicle driver core temperature to a temperature regulator. The temperature regulator determines whether the data describing the vehicle driver core temperature is similar to stored data describing one or more circadian temperatures associated with sleep. Responsive to determining that the data describing the vehicle driver core temperature is similar to a circadian temperature associated with drowsiness, the temperature regulator reduces the vehicle driver core temperature. In an embodiment, the temperature regulator cools a material which physically contacts a surface of the vehicle driver, such as the vehicle driver's palms, to a temperature lower than the vehicle driver's core temperature. In an embodiment, the cooled material physically contacts the venous plexuses and/or arteriovenous anastomoses, allowing the temperature regulator to most efficiently cool the vehicle driver. In an embodiment, the temperature regulator also includes a vacuum source which reduces the pressure in an area surrounding the cooled surface to further decrease the time needed to cool the driver by increasing the vehicle driver blood flow through the surface of the vehicle driver which physically contacts the cooled material.

In an embodiment, vehicle driver core temperature is initially determined. It is then determined whether the vehicle driver core temperature is a temperature associated with drowsiness. If the vehicle driver core temperature is associated with drowsiness, the vehicle driver core temperature is reduced. In an embodiment, the vehicle driver core temperature is reduced for a specified time interval. Alternatively, the vehicle driver core temperature is reduced until it reaches a specified core temperature, such as a core temperature associated with wakefulness.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

DETAILED DESCRIPTION OF THE INVENTION

Figure 1:
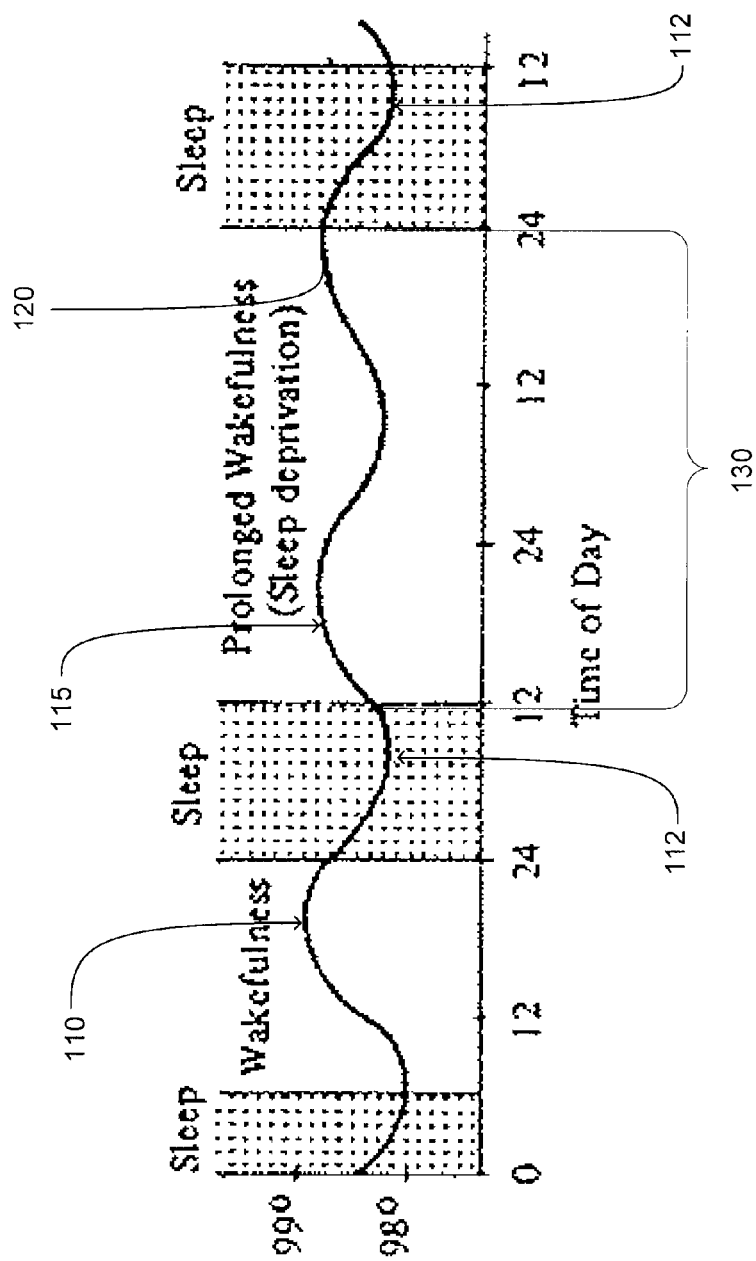
FIG. 1 is a graph illustrating the relationship between human body temperature and human sleep cycle.

A preferred embodiment of the present invention is now described with reference to the Figures where like reference numbers indicate identical or functionally similar elements. Also in the Figures, the left most digits of each reference number correspond to the Figure in which the reference number is first used.

Reference in the specification to "one embodiment" or to "an embodiment" means that a particular feature, structure, or characteristic described in connection with the embodiments is included in at least one embodiment of the invention. The appearances of the phrase "in one embodiment" in various places in the specification are not necessarily all referring to the same embodiment.

Some portions of the detailed description that follows are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or "determining" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions described herein in the form of an algorithm. It should be noted that the process steps and instructions of the present invention could be embodied in software, firmware or hardware, and when embodied in software, could be downloaded to reside on and be operated from different platforms used by a variety of operating systems.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein, and any references below to specific languages are provided for disclosure of enablement and best mode of the present invention.

In addition, the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention, which is set forth in the claims.

FIG. 1 shows the relationship between human body temperature and the human sleep cycle. As shown in FIG. 1, in a 24 hour period a human's core body temperature rises and falls in a rhythmic fashion. Even during periods of sleep deprivation 130, human core temperature maintains this rhythmic variation, commonly referred to as "circadian rhythm."

Studies have shown that elevated core temperature in the human body is associated with fatigue. Further, it has been observed that body temperature rises to a peak 110, 120 temperature before sleep onset. In fact, the human core temperature decreases after entering a sleep state and particularly during the so-called non-rapid eye movement (NREM) sleep state which is associated with passively decreased muscle tone. Throughout a sleep state, the body temperature reduces to a minimum value, or nadir, 112 when the person wakes up. Hence, variations in human core temperature affect the timing of sleep and wakefulness in humans. Because or this relationship between body temperature and sleep, affecting body temperature can prolong wakefulness in a person.

Because of the correlation between human core temperature peaks 110, 120 and the onset of drowsiness and the correlation between the human core temperature nadir 112 and awakening, reducing human core temperature as it approaches a peak 110, 120 may prevent the human from entering a drowsy state. However, the human body includes many physical mechanisms and systems which prevent external sources from rapidly or drastically modifying core temperature. In particular, the body includes a body thermostat in the preoptic anterior hypothalamus of the brain stem which triggers one or more mechanisms for maintaining body temperature. For example, in response to a rapid temperature drop, the body thermostat reduces blood flow to the body's extremities (e.g., hands and feet) to increase blood flow within the body's core. Conversely, the body thermostat dilates blood vessel to increase blood flow to the body's extremities to "cool" the body responsive to a rapid temperature increase. Other mechanisms exist in the human thermoregulation system to maintain a constant, regulated temperature.

Figure 2:
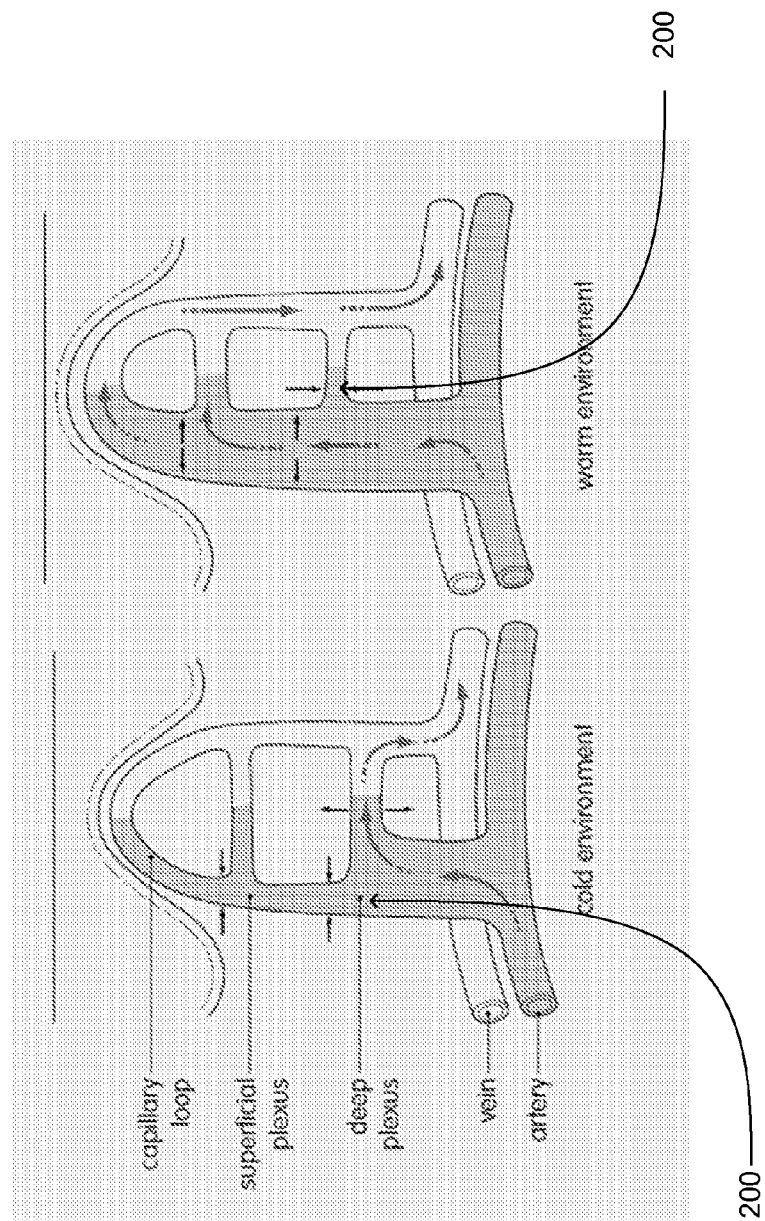
FIG. 2 is a diagram of the arteriovenous anastomoses of the human skin.

As part of the anatomical mechanisms to support this predisposition towards stabilizing core temperature, humans and other mammals include specialized blood vessels, such as venous plexuses and arteriovenous anastomoses which are capable of rapidly dissipating heat from the body. For purposes of illustration, FIG. 2 shows an illustration of the arteriovenous anastomoses 200 in the human body; however, the venous plexus have a similar structure and perform a similar function within the human body. The venous plexuses and arteriovenous anastomoses 200 are found in the palms, an area on the cheek below the eyelids and the soles of the feet. By redirecting blood from capillaries into the venous plexuses and/or arteriovenous anastomoses 200, the human body quickly dissipates heat. Hence, the venous plexuses and arteriovenous anastomoses 200 act as radiators for the human body to rapidly regulate core temperature.

However, the venous plexuses and arteriovenous anastomoses can also be used to heat or cool the body using the circulatory system. For example, applying an external heat source to the venous plexuses and arteriovenous anastomoses 200 warms the blood traveling through the venous plexuses and arteriovenous anastomoses 200 and causes the warmed blood to be returned to the heart. The circulatory system then circulates this warmed blood throughout the body, essentially warming the body from the inside out. Similarly, applying an external heat sink, such as a material cooled below the ambient temperature or temperature of the body, to the venous plexuses and/or arteriovenous anastomoses 200 extracts heat from blood circulating through the venous plexuses and arteriovenous anastomoses 200. The chilled blood is returned to the heart and circulated throughout the body by the circulatory system, allowing for rapid reduction in human core temperature. For example, applying a material cooled below ambient temperature or body temperature to the venous plexuses and arteriovenous anastomoses 200 allows heat to be extracted from the body at rates from 0.5 to 50 Kcal/min. Thus, application of a low temperature medium to the venous plexuses and/or arteriovenous anastomoses 200 enables rapid reduction of human core temperature.

Figure 3:
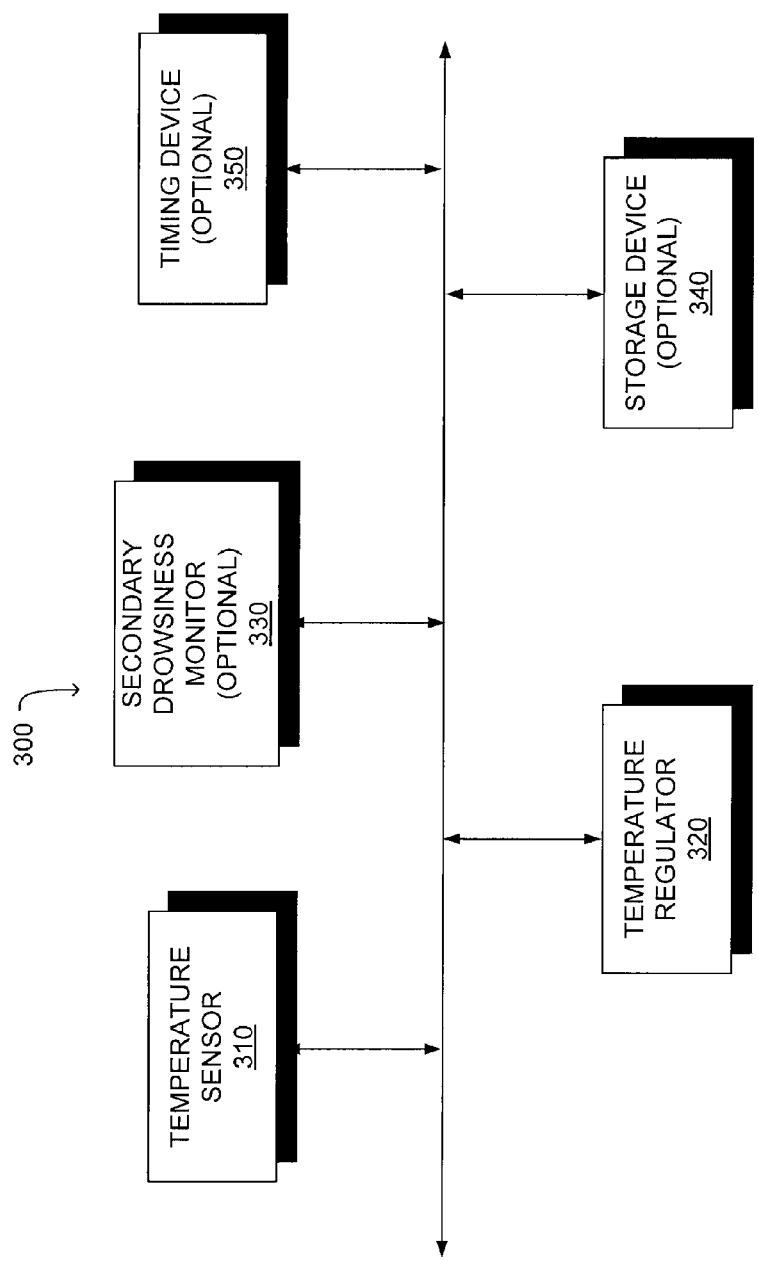
FIG. 3 is a computing system for regulating vehicle driver core temperature according to one embodiment of the invention.

FIG. 3 is a computer system 300 for regulating driver core temperature according to one embodiment of the invention. In one embodiment, the computer system 300 includes a temperature sensor 310 and a temperature regulator 320. In another embodiment, the computer system 300 also includes a secondary drowsiness monitor 330, a storage device 340 and/or a timing device 350.

The temperature sensor 310, such as a thermometer, captures data describing the temperature of a vehicle driver. In an embodiment, the temperature sensor 310 comprises an infrared or other non-invasive thermometer directed towards a vehicle driver which continuously captures data describing the vehicle driver's body temperature, which is used to calculate the vehicle driver's core temperature. Hence, the temperature sensor 310 allows non-invasive determination of the vehicle driver's core temperature. Alternatively, the temperature sensor 310 captures vehicle driver temperature data in periodic intervals. In various embodiments, the temperature sensor 310 comprises an infrared thermometer or other non-contact thermometer which captures data describing a vehicle driver temperature. For example, the temperature sensor 310 is attached to a vehicle side, a vehicle dashboard, included in a vehicle seat or other vehicle location having a line of sight to the vehicle driver. Alternatively, the temperature sensor 310 makes physical contact with a surface of the vehicle driver, such as the vehicle driver's ear or skin surrounding the ear, the vehicle driver's neck or other exposed skin on a vehicle driver, without interfering with the vehicle driver's ability to operate the vehicle. In another embodiment, the temperature sensor 310 is included in the temperature regulator 320, further described below, so that the temperature regulator 320 both determines the vehicle driver's temperature and modifies the vehicle driver's temperature.

The temperature regulator 320 makes contact with a surface of the vehicle driver, such as a portion of the vehicle driver's skin, such as the venous plexuses or arteriovenous anastomoses, and cools the vehicle driver. In one embodiment, the temperature regulator 320 comprises a material whose temperature is reduced to a temperature below the ambient temperature of the vehicle driver's. For example, the temperature regulator 320 includes aluminum or another material having high thermal conductivity coupled to a desiccant cooling device, an exothermic or endothermic chemical reaction or other device or reaction which produces a temperature variance. Alternatively, cooled liquid flows adjacent to a surface of the thermally conductive material, such as the surface which does not contact the vehicle driver's skin, and reduces the temperature of the thermally conductive material. Because the thermally conductive material contacts the venous plexuses or arteriovenous anastomoses of the vehicle driver, cooling the thermally conductive material extracts heat from the vehicle driver's circulating blood, reducing vehicle driver core temperature. In one embodiment, the thermally conductive material is included in a housing which is coupled to a vacuum source. The vacuum source reduces atmospheric pressure within the housing to a pressure lower than ambient pressure ("negative pressure"), to facilitate extraction of heat from the vehicle driver by increasing the amount of blood from the vehicle driver flowing through the venous plexuses and/or arteriovenous anastomoses. Examples of temperature regulator 320 implementations are found in U.S. Pat. Nos. 6,602,277, 6,656,208 and 6,974,442, where are incorporated by reference herein in their entirety.

In an embodiment, the computer system 100 also includes a secondary drowsiness monitor 330 which monitors the vehicle driver for one or more indications of drowsiness. For example, the secondary drowsiness monitor 330 comprises an image capture module which captures data describing how long the vehicle driver's eyes are closed during a blink, how a vehicle driver's head moves over time or other physiological data indicating a vehicle driver's alertness. Alternatively, the secondary drowsiness monitor 330 comprises a motion sensor monitoring vehicle motion to identify erratic driving patterns associated with drowsiness (e.g., swerving, wandering between locations). In another embodiment, the secondary drowsiness monitor 330 captures data describing vehicle steering performance (e.g., movement of a vehicle steering device such as a steering wheel, for example), which can be compared to road information stored in the storage device 340 to determine if the vehicle steering indicates vehicle driver drowsiness. For example, if the captured vehicle steering data deviates from the stored road information by a defined threshold, the captured steering data is associated with vehicle driver drowsiness.

The storage device 340 stores data from the temperature sensor 310, the secondary drowsiness monitor 330 and/or the temperature regulator 320. In an embodiment, the storage device 340 also stores data entered or provided by a user or other suitable manner of data acquisition. In an embodiment, the storage device 340 also stores data describing road information, such as maps also used for on-board navigation. The storage device 340 comprises a hard disk drive, a flash memory device or other suitable mass storage device. Further, the storage device 340 can be a volatile storage device (e.g., dynamic random access memory (DRAM), static random access memory (SRAM) or another suitable memory device), a non-volatile storage device or a combination of a non-volatile storage device and a volatile storage device.

In an embodiment, the computer system 300 also includes a timing device 350 which causes the temperature regulator 320 to reduce the vehicle driver's temperature at specified intervals or at specified times. For example, the timing device 350 includes data describing specified intervals in which to reduce the vehicle driver temperature, such as two hours after the vehicle is started. This allows vehicle driver temperature to be preemptively cooled before the vehicle driver exhibits symptoms of drowsiness. Alternatively, the timing device 350 includes data specifying one or more times to reduce vehicle driver temperature, such as cooling the vehicle driver at midnight or another time when the vehicle driver is likely to be drowsy. Additionally, the timing device 350 records data describing the duration of vehicle operation, such as the amount of time the vehicle has been running or moving.

It should be apparent to one skilled in the art that computing system 300 may include more or less components than those shown in FIG. 3 without departing from the spirit and scope of the present invention. For example, computing system 300 may include additional memory devices, such as, for example, a first or second level cache, or one or more application specific integrated circuits (ASICs). Similarly, computing system 300 may include additional input or output devices. In some embodiments of the present invention one or more of the components (310, 320, 330, 340, 350) can be positioned in close proximity to each other while in other embodiments these components can be positioned in different positions within a vehicle and communicate with each other using a wireless communication system, a wired communication system or a combination of wireless communication and wired communication systems. For example, the storage device 340 and/or the timing device 350 can be included in a vehicle trunk while the temperature sensor 310, temperature regulator 320 and secondary drowsiness monitor 330 are included in a vehicle passenger compartment.

Figure 4:
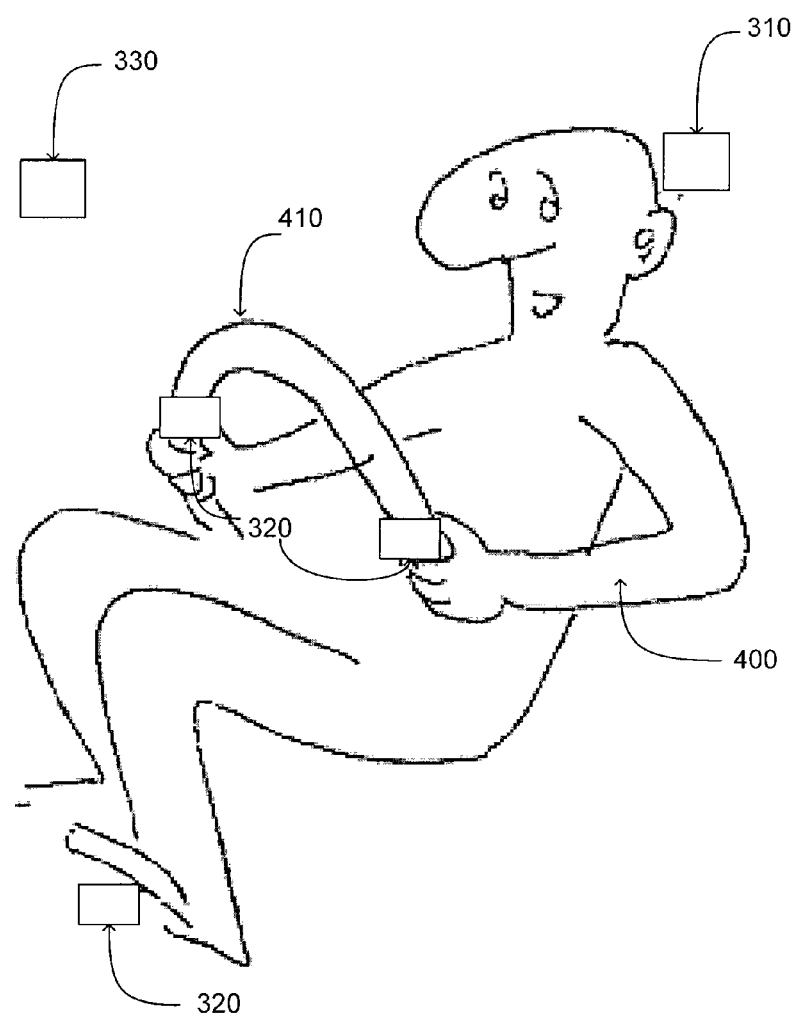
FIG. 4 is an example vehicle-based implementation of a vehicle driver core temperature regulation system according to an embodiment of the invention.

FIG. 4 is an example vehicle-based implementation of a driver core temperature regulation system according to an embodiment of the invention. For purposes of illustration, FIG. 4 shows the position of various components of the driver core temperature regulation system relative to a vehicle driver 400 in one embodiment. In other embodiments, the vehicle driver core temperature regulation system components are located in different positions relative to each other and the vehicle driver 400 within a vehicle.

In an embodiment, the temperature sensor 310 is located near the head of a vehicle driver 400. For example, the temperature sensor 310 is positioned near the vehicle driver's ear or forehead to determine the vehicle driver's temperature. The temperature sensor 310 communicates vehicle driver temperature data to the temperature regulator 320. For example, the temperature sensor 310 uses a wireless communication system such a as Bluetooth, WiFi or WiMAX transceiver to communicate temperature data to the temperature regulator 320. Alternatively, the temperature sensor 310 and temperature regulator 320 use a wired electrical or data connection to transmit and/or receive data.

The temperature regulator 320 physically contacts the venous plexuses and/or the arteriovenous anastomoses of the vehicle driver 400. This allows the temperature regulator 320 to more quickly and safely reduce the vehicle driver's 400 body temperature. While the temperature regulator 320 reduces vehicle driver core temperature at an increased rate, the temperature regulator 320 does not reduce the vehicle driver's core temperature rapidly enough for the vehicle driver's body to initiate defense mechanisms to regulate temperature. For example, while the temperature regulator 320 reduces the vehicle driver's temperature, this reduction in vehicle driver temperature does not cause the vehicle driver's body thermostat to constrict blood vessels or cause shivering to produce internal heat for maintaining vehicle driver core temperature. In the example illustrated in FIG. 4, a vehicle steering device 410, such as a steering wheel, includes the temperature regulator 320, so the temperature regulator 320 physically contacts the palms of the vehicle driver's 400 hands. Alternatively, a temperature regulator 320 physically contacts the soles of the vehicle driver's 400 feet and can be included in an accelerator pedal and/or a brake pedal of the vehicle. In another embodiment, the temperature regulator 320 physically contacts both the vehicle driver's palms and soles, allowing for more efficient cooling of the vehicle driver 400. These locations allow the temperature regulator 320 to most efficiently reduce vehicle driver 400 body temperature by exploiting regions of the vehicle driver's anatomy that most efficiently regulate temperature, such as the venous plexuses and arteriovenous anastomoses.

In an embodiment, the secondary drowsiness monitor 330 is positioned to capture video or image data of the vehicle driver's 400 face. For example, the secondary drowsiness monitor 330 is connected to a dashboard or other surface at the front of the vehicle. Alternatively, the secondary drowsiness monitor 330 communicates with a vehicle steering system and monitors changes in the vehicle's direction of motion. In another embodiment, the secondary drowsiness monitor 330 both captures data describing one or more physical attributes of the vehicle driver 400 and data describing the vehicle motion. In various embodiments, the secondary drowsiness monitor 330 uses a wireless communication method, a wired communication method or a combination of wireless and wired communication methods to exchange data with the temperature regulator 320 and/or the temperature sensor 310.

Figure 5:
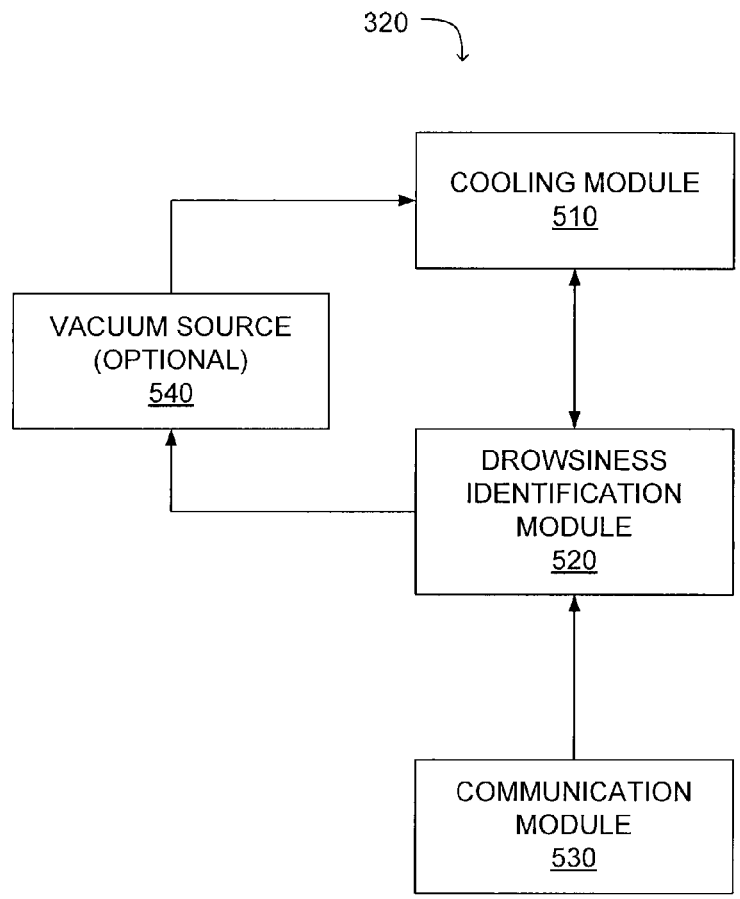
FIG. 5 is a temperature regulator according to an embodiment of the invention.

FIG. 5 shows a temperature regulator 320 according to an embodiment of the invention. The temperature regulator 320 comprises a cooling module 510, a drowsiness identification module 520 and a communication module 530. In an embodiment, the temperature regulator 320 further comprises a vacuum source 540.

The cooling module 510 comprises a material having high thermal conductivity, such as aluminum and a cooling system to reduce the temperature of the thermally conductive material. For example, the cooling module 510 includes a desiccant cooling device, reagents for an exothermic or endothermic chemical reaction or other device or reaction which reduces the temperature of the thermally conductive material. Alternatively, the cooling module 510 flows cooled liquid adjacent to a surface of the thermally conductive material. As the cooled liquid passes by the thermally conductive material, the temperature of the thermally conductive material is reduced as heat from the thermally conductive material flows from the material to the cooled liquid. For example, a vehicle driver physically contacts a first surface of the thermally conductive material while a second surface of the thermally conductive material is adjacent to the cooled liquid. Because the material is thermally conductive, cooling the second surface of the thermally conductive material also reduces the temperature of the first surface of the thermally conductive material. Hence, the cooling module 510 allows a surface of the thermally conductive material with a low temperature to physically contact a surface of the vehicle driver. As the cooling module 510 is positioned in the vehicle to physically contact the vehicle driver's venous plexuses or arteriovenous anastomoses, the cooling module 510 allows for rapid extraction of heat from the vehicle driver's body. Examples of a cooling module 510 are found in U.S. Pat. Nos. 6,602,277, 6,656,208 and 6,974,442, which are incorporated by reference herein in their entirety.

The drowsiness identification module 520 receives data from the communication module 530 describing vehicle driver temperature from the temperature sensor 310. The drowsiness identification module 520 compares the received vehicle driver temperature data with stored data to determine if the vehicle driver is drowsy or is likely to become drowsy. For example, the drowsiness identification module 520 compares vehicle driver temperature data to stored data describing human circadian rhythm temperatures. If the vehicle driver temperature data is similar to a circadian rhythm temperature associated with drowsiness is likely, the drowsiness identification module 520 communicates with the cooling module 510 to begin cooling the vehicle driver. Alternatively, the drowsiness identification module 520 uses temporal data from the communication module 530 to determine whether to begin cooling the vehicle driver. For example, the drowsiness identification module 520 compares data describing how long the vehicle has been moving or running or data identifying a time of day to stored data describing one or more times of day when a vehicle driver is likely to be drowsy or describing a threshold value representing an operating time when the vehicle driver is likely to become drowsy. In an embodiment, the drowsiness identification module 520 also receives data from the secondary drowsiness monitor 330 and determines whether the received data is similar to store data describing physical characteristics or vehicle movement associated with drowsiness.

The drowsiness identification module 520 can be implemented in many ways. For example, it can be a software process executable by processor (not shown) and/or a firmware application. The process and/or firmware can be configured to operate on a general purpose microprocessor or controller, a field programmable gate array (FPGA), an application specific integrated circuit (ASIC) or a combination thereof. Alternatively, the drowsiness identification module 520 comprises a processor configured to process data describing events and may comprise various computing architectures including a complex instruction set computer (CISC) architecture, a reduced instruction set computer (RISC) architecture or an architecture implementing a combination of instruction sets. The drowsiness identification module 520 can comprise a single processor or multiple processors. Alternatively, drowsiness identification module comprises multiple software or firmware processes running on a general purpose computer hardware device.

The communication module 530 links the drowsiness identification module 520 to the temperature sensor 310, the secondary drowsiness monitor 330, the storage device 340 and/or other vehicle systems or systems external to the vehicle via a network (not shown). The network may comprise a local area network (LAN), a wide area network (WAN) (e.g. the Internet), and/or any other interconnected data path across which multiple devices may communicate. In one embodiment, the communication module 530 is a conventional connection, such as USB, IEEE 1394 or Ethernet, to one or more vehicle systems or external systems for distribution of files and information. In another embodiment, the communication module 530 is a conventional type of transceiver, such as for infrared communication, IEEE 802.11a/b/g/n (or WiFi) communication, Bluetooth® communication, 3 G communication, IEEE 802.16 (or WiMax) communication, or radio frequency communication.

In one embodiment, the temperature regulator 320 also includes a vacuum source 540 which communicates with the cooling module 510 and the drowsiness identification module 520. The vacuum source reduces the atmospheric pressure in an area adjacent to the cooling module 510 to increase vehicle driver blood flow through the surface or surfaces physically contacting the cooling module 510. For example, the cooling module 510 includes a housing or casing surrounding the thermally conductive material which is connected to the vacuum source 540. The vacuum source 540 reduces atmospheric pressure within the housing or casing to a pressure lower than ambient pressure ("negative pressure"), allowing the thermally conductive material to more rapidly extract heat from the vehicle driver. Any type of vacuum regulator or control mechanism may be used to modify the pressure associated with the cooling module 510. Examples of temperature regulator 320 implementations are found in U.S. Pat. Nos. 6,602,277, 6,656,208 and 6,974,442, where are incorporated by reference herein in their entirety.

Figure 6:
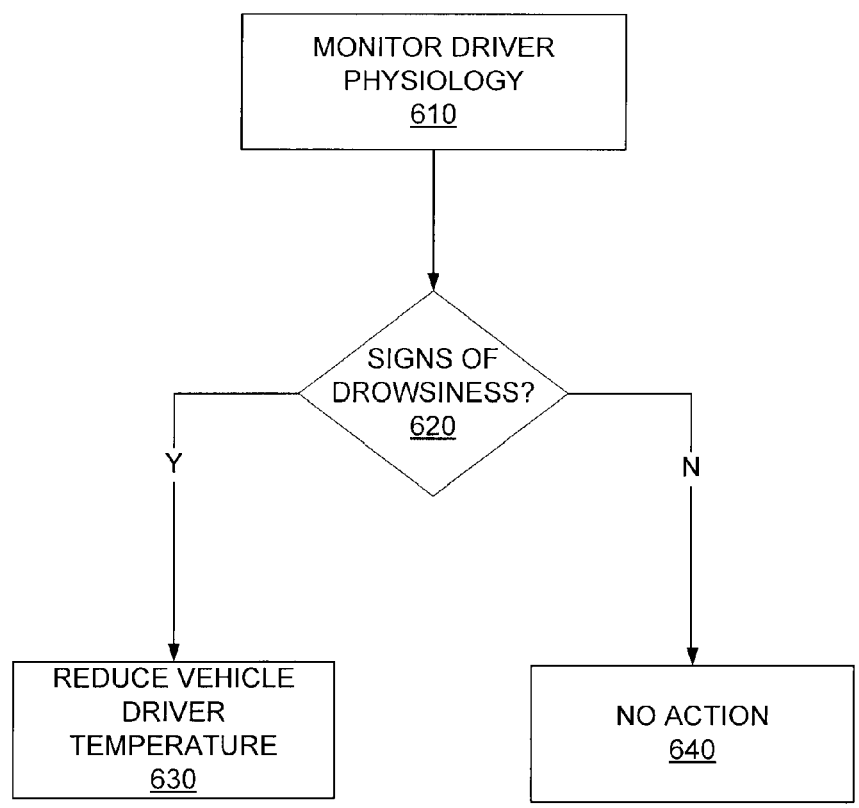
FIG. 6 is a flowchart of a method for regulating vehicle driver temperature based on drowsiness detection according to an embodiment of the invention.

FIG. 6 is a flowchart of a method for regulating vehicle driver temperature based on drowsiness detection according to an embodiment of the invention.

Initially, the temperature sensor 310 monitors 610 the vehicle driver's temperature. In an embodiment, the vehicle driver's temperature is continuously monitored 610 by the temperature sensor 310. Alternatively, the temperature sensor 310 measures the vehicle driver's temperature at specified intervals. For example, the temperature sensor 310 measures vehicle driver temperature at one hour intervals, two hour intervals or after a predefined duration. In an embodiment, temperature sensor 310 also determines the time of day from a vehicle clock and adjusts the vehicle driver monitoring 610 based on the time of day. For example, between 6 PM and 6 AM, the vehicle driver temperature is monitored 610 more frequently (e.g., at 30 minute intervals), as the vehicle driver is more likely to be drowsy. Alternatively, the vehicle driver monitoring 610 increases in frequency as the vehicle driver temperature increases.

Additionally, in an embodiment, the secondary drowsiness monitor 330 also monitors 610 the vehicle driver for physiological signs of drowsiness. For example, the secondary drowsiness monitor determines the vehicle driver's gaze stability, how frequently the vehicle driver blinks, how long the vehicle driver's eyes are closed when blinking, the vehicle driver's head movement, movement of the vehicle driver's hands or other physical actions of the vehicle driver associated with drowsiness. This allows the secondary drowsiness monitor 330 to monitor 610 additional physical characteristics of the vehicle driver to more accurately determine if the vehicle driver is drowsy.

The temperature regulator 320 then receives data from the temperature sensor 310 and/or the secondary drowsiness monitor 330 and determines 620 whether the received data is associated with one or more signs of vehicle driver drowsiness. For example, the temperature regulator 320 determines 620 whether the vehicle driver's temperature equals a maximum vehicle driver temperature or whether the vehicle driver's temperature is within a threshold amount of the maximum vehicle driver temperature. In an embodiment, the temperature regulator 320 also evaluates data from the secondary drowsiness monitor 330 to determine 620 whether the vehicle driver is exhibiting one or more physical behaviors associated with drowsiness.

If the temperature regulator 320 determines 620 that the vehicle driver is exhibiting one or more signs of drowsiness, the temperature regulator 320 reduces 630 the vehicle driver's core temperature. Hence, if the vehicle driver is exhibiting one or more physical behaviors commonly associated with drowsiness, the vehicle driver's temperature is reduced to increase the vehicle driver's alertness. As the human body associates lower core temperatures with wakefulness, by reducing the vehicle driver's temperatures, the temperature regulator 320 increases the likelihood that the vehicle driver will remain awake and alert. In one embodiment, the temperature regulator 320 cools the vehicle driver for a specified or predetermined time interval. Alternatively, the temperature regulator cools the driver to a predetermined temperature, such as the circadian rhythm nadir. However, if the temperature regulator determines 6230 that the vehicle driver is not exhibiting signs of drowsiness, no action is taken 640 by the temperature regulator so the vehicle driver's temperature is unchanged.

Figure 7:
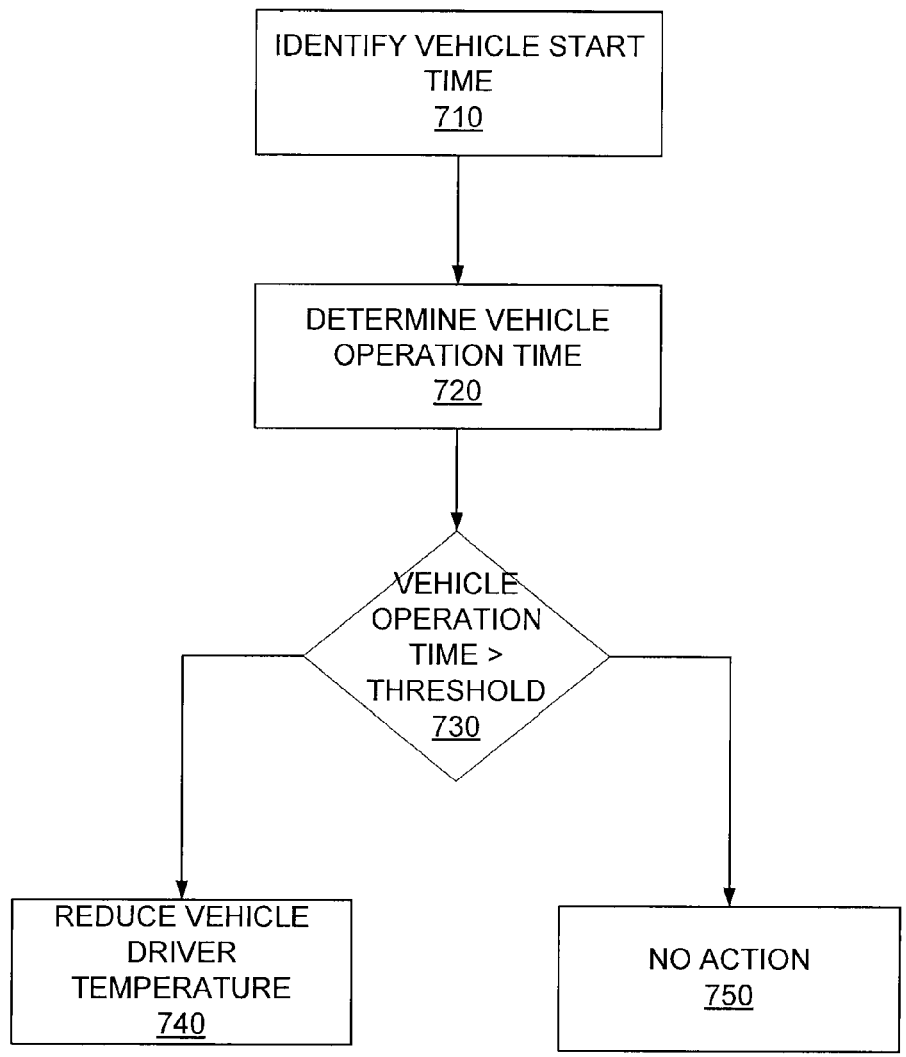
FIG. 7 is a flowchart of a method for regulating vehicle driver temperature based on vehicle operation time according to an embodiment of the invention.

FIG. 7 is a flowchart of a method for regulating vehicle driver temperature based on vehicle operation time according to an embodiment of the invention.

Initially, the temperature regulator 320 or timing device 350 identifies 710 the vehicle start time. In an embodiment, the time in which the vehicle starts moving is identified 710 as the vehicle start time. Alternatively, the time when a vehicle component, such as an engine or drive train component, begins operating is identified 710 as the vehicle start time. The vehicle operation time is then determined 720 with reference to the vehicle start time. For example, when the vehicle is started, a timer which indicates time elapsed from the vehicle start time. In an embodiment, the timing device 350, storage device 340 or temperature regulator 320 stores data describing the vehicle operation time.

The temperature regulator 320 then determines 730 whether the vehicle operation time exceeds a threshold value stored in the storage device or the temperature regulator 320. In an embodiment, the threshold value represents a time interval in which it is likely for a vehicle driver to become fatigued, such as three hours of vehicle operation. In an embodiment, the threshold value can be customized according to various user implementations, preferences or requirements. If the vehicle operation time exceeds or equals the threshold value, the temperature regulator 320 reduces 740 the vehicle driver's core temperature Hence, after the vehicle driver operates the vehicle for an amount of time specified by the threshold value, the temperature regulator 320 reduces the vehicle driver's temperature to increase the vehicle driver's alertness. As vehicle operators are likely to become drowsy after operating a vehicle for long periods of time, reducing the vehicle driver's core to a temperature the human body associates with wakefulness, the temperature regulator 320 increases the likelihood that the vehicle driver will remain awake and alert. In one embodiment, the temperature regulator 320 cools the vehicle driver for a specified or predetermined time interval. Alternatively, the temperature regulator cools the driver to a predetermined temperature, such as the circadian rhythm nadir. However, if the temperature regulator determines that the vehicle operating time is less than the threshold value, no action is taken 640 by the temperature regulator 320 so the vehicle driver's temperature is unchanged.

While particular embodiments and applications of the present invention have been illustrated and described herein, it is to be understood that the invention is not limited to the precise construction and components disclosed herein and that various modifications, changes, and variations may be made in the arrangement, operation, and details of the methods and apparatuses of the present intervention without departing from the spirit and scope of the invention as it is defined in the appended claims.

What is claimed is:

1. A vehicle-based system for reducing a core temperature of a vehicle driver in a vehicle comprising:
    a temperature sensor capturing data describing the core temperature of the vehicle driver, the temperature sensor located within a steering wheel of the vehicle and making physical contact with exposed skin of the vehicle driver; and
    a temperature regulator adapted to communicate with the temperature sensor, the temperature regulator analyzing the data describing the core temperature of the vehicle driver to determine when there is a rise in the core temperature of the vehicle driver, and the temperature regulator comprising a surface in physical contact with the driver, the temperature regulator cooling the surface to a temperature below an ambient temperature of the vehicle responsive to the data describing the risen core temperature of the vehicle driver equaling or exceeding a temperature associated with sleep onset.

2. The vehicle-based system of claim 1, further comprising:
    a secondary drowsiness monitor adapted to communicate with the temperature regulator, the secondary drowsiness monitor capturing data describing one or more vehicle driver actions.

3. The vehicle-based system of claim 2, wherein the one or more vehicle driver actions comprise a head movement, a blink rate, a blink duration, a gaze stability or a steering device movement.

4. The vehicle-based system of claim 1, wherein the surface of the temperature regulator is located on a surface of a steering device of the vehicle.

5. The vehicle-based system of claim 1, wherein cooling the surface comprises cooling a thermally conductive material in contact with a palm of the vehicle driver.

6. The vehicle-based system of claim 1, further comprising:
    a storage device adapted to communicate with the temperature regulator, the storage device storing the temperature associated with sleep onset.

7. The vehicle-based system of claim 1, further comprising:
    a timing device adapted to communicate with the temperature regulator, the timing device capturing data describing a vehicle operation time.

8. The vehicle-based system of claim 7, wherein the temperature regulator compares the data describing the vehicle operation time to a threshold operation time and the temperature regulator cools the surface responsive to the data describing the vehicle operation time equaling or exceeding the threshold operation time.

9. The vehicle-based system of claim 3, wherein the temperature regulator compares the data describing the steering device movement to stored navigation data and responsive to the data describing the steering device movement differing from the stored navigation data by a specified threshold, the temperature regulator cools the surface.

10. A computer-implemented method for reducing a core temperature of a vehicle driver in a vehicle comprising:
    determining the core temperature of the vehicle driver via a temperature sensor located within a steering wheel of the vehicle and making physical contact with exposed skin of the vehicle driver;
    determining whether the core temperature of the vehicle driver equals or exceeds a temperature associated with sleep onset; and
    responsive to determining the core temperature of the vehicle driver equals or exceeds the temperature associated with sleep onset, cooling a surface of a steering device of the vehicle that is in physical contact with the vehicle driver to a temperature below an ambient temperature of the vehicle.

11. The computer-implemented method of claim 10, wherein cooling the surface of the steering device comprises:
    reducing a surface temperature of a thermally conductive material in contact with a palm of the vehicle driver.

12. The computer-implemented method of claim 11, further comprising:
    reducing a pressure of an area adjacent to the thermally conductive material to a value less than an ambient air pressure.

13. The computer-implemented method of claim 10, further comprising:
    receiving data describing one or more driver actions;

determining whether the one or more driver actions are associated with drowsiness; and cooling the surface of the steering device of the vehicle responsive to determining that the one or more driver actions are associated with drowsiness.

14. The computer-implemented method of claim 13, wherein the one or more driver actions comprise a head movement, a blink rate, a blink duration, a gaze stability or a steering device movement.

15. The computer-implemented method of claim 10, further comprising:

determining a cooled vehicle driver core temperature;

comparing the cooled vehicle driver core temperature to a circadian rhythm temperature associated with wakefulness; and responsive to the cooled vehicle driver core temperature not exceeding the temperature associated with wakefulness, stopping reducing the core temperature of the vehicle driver.

16. An apparatus for reducing a core temperature of a vehicle driver comprising:

a cooling module including a thermally conductive surface, the thermally conductive surface having a first side physically contacting the vehicle driver;

a drowsiness identification module adapted to communicate with the cooling module, the drowsiness identification module receiving data describing the core temperature of the vehicle driver from a temperature sensor located within a steering wheel of the vehicle and making physical contact with exposed skin of the vehicle driver, comparing the data describing the core temperature of the vehicle driver with data describing one or more circadian rhythm temperatures associated with sleep and, responsive to the data describing the core temperature of the vehicle driver equaling or exceeding a circadian rhythm temperature associated with sleep, transmitting a cooling signal to the cooling module, causing the cooling module to reduce a temperature of the thermally conductive surface to a temperature below an ambient temperature of the vehicle.

17. The vehicle-based system of claim 5 wherein the temperature regulator cools the surface of to a temperature below an average vehicle driver's core temperature.

18. The computer-implemented method of claim 11 wherein the thermally conductive material is cooled to a temperature below an average vehicle driver's core temperature.

* * * * *